(12) United States Patent
Paik et al.

(10) Patent No.: US 9,116,152 B2
(45) Date of Patent: Aug. 25, 2015

(54) MONOCLONAL ANTIBODIES WHICH SPECIFICALLY RECOGNIZE HUMAN LIVER-CARBOXYLESTERASE 1, HYBRIDOMA CELL LINES WHICH PRODUCE MONOCLONAL ANTIBODIES, AND USES THEREOF

(75) Inventors: Young Ki Paik, Seoul (KR); Keun Na, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 39 days.

(21) Appl. No.: 14/112,411

(22) PCT Filed: Apr. 17, 2012

(86) PCT No.: PCT/KR2012/002911
§ 371 (c)(1),
(2), (4) Date: Feb. 19, 2014

(87) PCT Pub. No.: WO2012/144784
PCT Pub. Date: Oct. 26, 2012

(65) Prior Publication Data
US 2014/0154699 A1 Jun. 5, 2014

(30) Foreign Application Priority Data

Apr. 18, 2011 (KR) .......... 10-2011-0035619
Apr. 4, 2012 (KR) .......... 10-2012-0034928

(51) Int. Cl.
| | | |
|---|---|---|
| *G01N 33/53* | (2006.01) | |
| *G01N 33/573* | (2006.01) | |
| *C07K 16/00* | (2006.01) | |
| *C07K 16/40* | (2006.01) | |
| *G01N 33/574* | (2006.01) | |

(52) U.S. Cl.
CPC .............. *G01N 33/573* (2013.01); *C07K 16/40* (2013.01); *G01N 33/57438* (2013.01); *C07K 2317/34* (2013.01); *G01N 2333/918* (2013.01)

(58) Field of Classification Search
CPC ..... G01N 33/53; G01N 33/573; C07K 16/00; C07K 16/40
USPC ................ 435/7.1, 7.4, 326, 338; 530/388.1, 530/388.26
See application file for complete search history.

(56) References Cited

U.S. PATENT DOCUMENTS

2011/0097738 A1* 4/2011 Paik et al. .............. 435/7.4

FOREIGN PATENT DOCUMENTS

| JP | 2002142780 | 5/2002 |
|---|---|---|
| KR | 1020090098366 | 9/2009 |
| WO | WO-2008066964 A2 | 6/2008 |
| WO | WO-2009077479 A2 | 6/2009 |

OTHER PUBLICATIONS

Extended European Search Report issued in European Application No. 12774256.7 dated Nov. 5, 2014.
Na et al. "Human Plasma Carboxylesterase 1, a Novel Serologic Biomarker Candidate for Hepatocellular Carcinoma." *Proteomics.* 9(2009):3989-3999.

\* cited by examiner

*Primary Examiner* — Yan Xiao
(74) *Attorney, Agent, or Firm* — Mintz Levin Ferris Glovsky and Popeo, P.C.; Fred Hernandez; Shovon Ashraf (57) ABSTRACT

The present invention relates to monoclonal antibodies which specifically recognize human liver-carboxylesterase 1, hybridoma cell lines which produce monoclonal antibodies, and uses thereof. The invention can be used for the objective analysis of the expression amount of human liver-carboxylesterase 1 in tissues and blood, and the like, by being specifically bound to the human liver-carboxylesterase 1. Therefore, liver cancer can be conveniently and quickly diagnosed from urine or blood.

8 Claims, 4 Drawing Sheets

MONOCLONAL ANTIBODIES WHICH SPECIFICALLY RECOGNIZE HUMAN LIVER-CARBOXYLESTERASE 1, HYBRIDOMA CELL LINES WHICH PRODUCE MONOCLONAL ANTIBODIES, AND USES THEREOF

CROSS-REFERENCE TO RELATED APPLICATION

This application claims priority to and the benefit of Korean Patent Application No. 2011-0035619 and 2012-0034928, filed Apr. 18, 2011 and Apr. 4, 2012, respectively, the disclosures of which are incorporated herein by reference in their entirety.

INCORPORATION-BY-REFERENCE OF SEQUENCE LISTING

The contents of the text file named "46278-504N01US_ST25.txt", which was created on Oct. 17, 2013 and is 1.06 KB in size, are hereby incorporated by reference in their entireties.

BACKGROUND

1. Field of the Invention

The present invention relates to a monoclonal antibody specifically recognizing a human liver-carboxylesterase 1 which can be used to objectively analyze an expression level of the human liver-carboxylesterase 1 from human clinical specimens, such as a tissue and the blood, a hybridoma cell line producing the antibody, and its use thereof.

2. Discussion of Related Art

A human carboxylesterase (hCE) may be mainly classified as isoform having different properties and structures such as a human carboxylesterase 1 (hCE1), a human carboxylesterase 2 (hCE2), and a human carboxylesterase 3 (hCE3). (Imai T, *Drug Metab Pharmacokinet.*, vol. 21, pp. 173-185, 2006). The hCE1 is an enzyme generally biosynthesized in the liver and recognizing an acyl group of a hydrophilic molecule to decompose a chemical material absorbed into a tissue. However, the hCE2 is an enzyme generally expressed in the intestine, which is a separate protein having homology to the hCE1 of 47%, and reacting with an acyl group of a hydrophobic molecule absorbed into the intestine. The hCE3 is an enzyme generally expressed in the brain, which may also be a separate protein having homology to the hCE1 of 50%.

A liver-carboxylesterase 1 is an enzyme expressed in the liver, intestine, kidney, lung, heart, or macrophage, but is expressed in the liver 10 to 100 times higher than in the others. The liver-carboxylesterase 1 has three major roles: First, it has a function of xenobiotic metabolism which converts an inactive drug input into a human body into an active drug by modifying ester or amide structure of the inactive drug. For example, lovastatin is converted into an active form to reduce cholesterol, and serves to convert cocaine and heroin, which are toxic in the body, into non-toxic cocaethylene and morphine, respectively. Second, it can regulate cholesterol metabolism by decomposing and binding to an ester structure of cholesterol and a fatty acid in the body as needed, and third, it serves to regulate a function by directly binding to a protein, that is, C-reactive protein (CPR), recognizing the immunization of a macrophage in an endoplasmic reticulum (Redinbo M R., *Biochem. Soc. Trans.*, 31, pp. 620-624, 2003; Redinbo M R., *Drug Discov. Today.*, 10, pp. 313-325, 2005). Another property of the liver-carboxylesterase 1 is that its enzymatic activity is drastically decreased in a liver microsome of a rat in which a liver cancer is induced by a chemical material (Maki T., *Jpn. J. Cancer Res.*, 82, pp. 800-806, 1991), and a mechanism thereof is not discovered yet.

Until now, a degree of activity of a liver-carboxylesterase 1 in vivo was analyzed as an enzyme titration value using a non-specific substrate of an esterase enzyme, such as p-nitrophenylphosphate or p-nitrophenylacetate. According to such a method, it is impossible to measure specific activity of only the liver-carboxylesterase 1, because albumin, acetylcholinesterase, butyrylcholinesterase, etc. having a function of an esterase in the blood also have the same activities (Li B., *Niochem. Pharmacol.*, 70, pp. 1673-1684, 2005). Thus, a method capable of selectively and effectively analyzing a liver-carboxylesterase 1 protein from a large amount of specimens for a short time is needed, and such a method is enzyme immunoassay. The enzyme immunoassay is a method of inducing antigen-antibody binding through a reaction of an antibody binding to a desired protein (antigen), and quantifying a desired protein in a clinical specimen from coloring or fluorescence produced by a binding degree in a reaction to form a complex between an enzyme binding to an antibody and a substrate.

Recently, the inventors proved the presence of a liver-carboxylesterase 1 in a human plasma, and that an expression level of the liver-carboxylesterase 1 was increased by 2.8 times or more on average in the plasma of a liver cancer patient, compared to in the plasma of a normal person, while an expression level of the liver-carboxylesterase 1 was decreased in a liver cancer tissue, compared to that in a normal liver tissue (Na K. et al., *Proteomics.* 9, pp. 3989-3999, 2009). However, an antibody of the liver-carboxylesterase 1 used in the experiment is a commercially available polyclonal antibody (Abcam, ab1875), to which non-specific proteins can bind, and which is decreased in immunoprecipitation efficiency.

SUMMARY OF THE INVENTION

The present invention is directed to providing a monoclonal antibody of a liver-carboxylesterase 1 effectively analyzing a liver-carboxylesterase 1 in a tissue or the blood, and a hybridoma cell line producing the antibody.

The present invention is also directed to providing use of the antibody for isolating and purifying the liver-carboxylesterase 1, and detecting the liver-carboxylesterase 1 from the blood, and specifically diagnosing liver cancer.

One aspect of the present invention provides a monoclonal antibody specifically binding to a human liver-carboxylesterase 1 protein produced by a hybridoma deposited under Accession No. KCLRF-BP-00282.

Another aspect of the present invention provides a hybridoma cell deposited under Accession No. KCLRF-BP-00282, which produces the monoclonal antibody of the present invention.

Still another aspect of the present invention provides a composition for isolating and purifying a human liver-carboxylesterase 1 protein, comprising the monoclonal antibody of the present invention.

Yet another aspect of the present invention provides a composition for detecting a human liver-carboxylesterase 1, comprising the monoclonal antibody of the present invention.

Yet another aspect of the present invention provides a method of detecting a concentration of a human liver-carboxylesterase 1 in the urine or blood, comprising detecting the formation of an antigen-antibody complex by contacting the monoclonal antibody of the present invention with a sample.

Yet another aspect of the present invention provides a kit for diagnosing liver cancer, comprising the monoclonal antibody of the present invention.

BRIEF DESCRIPTION OF THE DRAWINGS

The above and other objects, features, and advantages of the present invention will become more apparent to those of ordinary skill in the art by describing in detail exemplary embodiments thereof with reference to the attached drawings, in which.

DETAILED DESCRIPTION OF EXEMPLARY EMBODIMENTS

Hereinafter, exemplary embodiments of the present invention will be described in detail. However, the present invention is not limited to the embodiments disclosed below, but can be implemented in various forms. The following embodiments are described in order to enable those of ordinary skill in the art to embody and practice the present invention.

Although the terms first, second, etc. may be used to describe various elements, these elements are not limited by these terms. These terms are only used to distinguish one element from another. For example, a first element could be termed a second element, and, similarly, a second element could be termed a first element, without departing from the scope of exemplary embodiments. The term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

The terminology used herein is for the purpose of describing particular embodiments only and is not intended to be limiting of exemplary embodiments. The singular forms "a," "an," and "the" are intended to include the plural forms as well, unless the context clearly indicates otherwise. It will be further understood that the terms "comprises," "comprising," "includes," and/or "including," when used herein, specify the presence of stated features, integers, steps, operations, elements, components, and/or groups thereof, but do not preclude the presence or addition of one or more other features, integers, steps, operations, elements, components, and/or groups thereof.

With reference to the appended drawings, exemplary embodiments of the present invention will be described in detail below. To aid in understanding the present invention, like numbers refer to like elements throughout the description of the figures, and the description of the same elements will be not reiterated.

The inventors have accomplished the present invention by developing a monoclonal antibody having higher efficiency than a commercially available antibody of a human liver-carboxylesterase 1 and a hybridoma cell line producing the antibody, to be used as means for isolating a liver-carboxylesterase 1 in the plasma and objectively comparatively analyzing an amount of the enzyme.

Accordingly, the present invention provides a monoclonal antibody specifically binding to a human liver-carboxylesterase 1 protein produced by a hybridoma, which is deposited under Accession No. KCLRF-BP-00282, a hybridoma cell producing the monoclonal antibody, and a method of preparing the same.

The "human liver-carboxylesterase 1" used herein includes a protein itself, a gene recombinant protein thereof, an artificial mutant and mutant thereof, a natural type of a protein, and a functional equivalent thereof.

The monoclonal antibody specific to a human liver-carboxylesterase 1 of the present invention may be prepared by a fusion method well known in the art (refer to Kohler and Milstein (1976) *European Journal of Immunology* 6:511-519). As one of two cell groups fused to form a "hybridoma" secreting the monoclonal antibody, a cell of an immunologically suitable host animal such as a mouse into which the human liver-carboxylesterase 1 is injected is used, and as the other group, a cancer or myeloma cell line is used. Cells of these two groups are fused by a method known in the art such as polyethyleneglycol, and then an antibody-producing cell is proliferated by a standard tissue culture method. A uniform cell group is yielded by subcloning by a limited dilution technique, and then a hybridoma cell line capable of producing an antibody specific to the human liver-carboxylesterase 1 is selected by enzyme-linked immunosorbent assay (ELISA) or western blotting, and incubated in large amounts in vitro or in vivo according to a standard technique. The in vivo bulk incubation means the isolation of the hybridoma cell line from ascites after production of a high concentration of antibodies is induced by injecting the hybridoma cell line into an abdominal cavity of a mouse.

The monoclonal antibody produced by the hybridoma cell line may not be purified, or purified at a high purity (e.g., 95% or more) according to a method well known in the art. The monoclonal antibody may be isolated from a culture medium or ascites using such a purification technique, for example, gel electrophoresis, dialysis, salt precipitation, ion exchange chromatography, or affinity antigen column chromatography.

A hybridoma producing a monoclonal antibody according to the present invention was named a hybridoma YPRC 10E8, and deposited to Korean Cell Line Research Foundation, which is the international deposition organization in Cancer Research Institute of the medical school of Seoul National University located in Yeungun-dong Jongro-gu, Seoul, under Accession No. KCLRF-BP-00282 on Mar. 28, 2012. In the specification, a monoclonal antibody produced by the "hybridoma YPRC 10E8" was named "YPRC 10E8."

An advantage obtained when the monoclonal antibody is used to detect an antigen is that the monoclonal antibody has a specific interaction by recognizing a single epitope. To map an epitope involved in the interaction between an antigen and an antibody, various approaches may be used. For example, such various approaches include biopanning using a phage display peptide library, determination of a fragment including an epitope sequence by being screened by immunoblotting a fragment produced by decomposing an antigen polypeptide with a protease, screening a peptide array fixed on a solid such as an activated membrane or a polyethylene pin, and competitive ELISA using a soluble peptide to prove importance of each amino acid sequence residue in the epitope sequence.

The epitope on the human liver-carboxylesterase 1 recognized by the monoclonal antibody of the present invention was analyzed from a three-dimensional structure of the human liver-carboxylesterase 1 using software produced by AbFrontier to examine that it was different from an amino acid sequence of a corresponding protein of an immunized mouse from an analyzed peptide list. Then, the epitope was determined by reselecting based on a peptide specific to the analyzed human liver-carboxylesterase 1.

A linear epitope set forth in SEQ ID NO: 1 corresponding to amino acids 554 to 567 at the C-terminal of the amino acid sequence of the human liver-carboxylesterase 1 based on such an epitope could be designated.

Antigen binding affinity of the monoclonal antibody may be determined according to a conventional method, but the present invention is not limited thereto. More particularly, the binding affinity with an antigen is measured by radioimmunoassay (RIA), enzyme immunoassay (ELISA), immunoprecipitation, an immunofluorescence method, a colored particle binding method, a chemical luminous material binding method, or immunoblotting. The monoclonal antibody of the present invention has a binding affinity over 20 times higher than that of a polyclonal antibody.

The monoclonal antibody according to the present invention may be an immunoglobulin isotype of IgG1.

Thus, the present invention provides a monoclonal antibody recognizing a linear epitope set forth in SEQ ID NO: 1 corresponding to amino acids 554 to 567 of the C-terminal of the amino acid sequence of the human liver-carboxylesterase 1 of the present invention to specifically bind to the human liver-carboxylesterase 1.

The term "monoclonal antibody" used herein is the term known in the art, meaning a highly specific antibody directing to a single antigenic site. Conventionally, in contrast to a polyclonal antibody including different antibodies directing to different epitopes (antigenic determinants), the monoclonal antibody directs to a single determinant on an antigen. The monoclonal antibody improves selectivity and specificity of diagnostic and analytical methods using antigen-antibody binding, and is not contaminated by a different immunoglobulin since it is synthesized by hybridoma culture. In the specification, the monoclonal antibody, as the antibody with respect to the human liver-carboxylesterase 1, includes a functional fragment of an antibody molecule as well as an entire antibody. The entire antibody has a structure having two full length light chains and two full length heavy chains, and each light chain is connected to the heavy chain by a disulfide bond. A heavy chain constant domain is a gamma ($\gamma$), mu ($\mu$), alpha ($\alpha$), delta ($\delta$), or epsilon ($\epsilon$) type, which is classified into sub-classes such as gamma 1 ($\gamma$1), gamma2 ($\gamma$2), gamma3 ($\gamma$3), gamma4 ($\gamma$4), alpha1 ($\alpha$1), and alpha2 ($\alpha$2). A light chain constant domain is a kappa ($\kappa$) or ramda ($\lambda$) type (Cellular and Molecular Immunology, Wonsiewicz, M. J., Ed., Chapter 45, pp. 41-50, W. B. Saunders Co. Philadelphia, Pa. (1991); Nisonoff, A., Introduction to Molecular Immunology, 2nd Ed., Chapter 4, pp. 45-65, Sinauer Associates, Inc., Sunderland, Mass. (1984)).

The functional fragment of the antibody molecule is a fragment having an antigen-binding function, including Fab, F(ab'), F(ab')2, and Fv. Fab of the antibody fragment is a structure having variable domains of a light chain and a heavy chain, a constant domain of the light chain, and a first constant domain (CH1) of the heavy chain, and has one antigen-binding site. Fab' is different from Fab in that it has a hinge region including at least one cysteine residue at the C terminal of the heavy chain CH1 domain. An F(ab')2 antibody has a disulfide bond formed by cysteine residues in the hinge region of the Fab'. Fv is a minimal antibody segment only having a heavy chain variable domain and a light chain variable domain, and a recombinant technique producing an Fv fragment is disclosed in WO 88/10649, WO 88/106630, WO 88/07085, WO 88/07086, and WO 88/09344. In disulfide-stabilized Fv (dsFv), a heavy chain variable domain and a light chain variable domain are generally connected by a non-covalent bond, and in single chain Fv (scFv), a heavy chain variable domain and a light chain variable domain are generally connected by a covalent bond via a peptide linker, or directly connected to the C-terminal, thereby forming a structure such as a dimer like dsFv.

Such an antibody fragment may be obtained using a protein hydrolase (for example, Fab may be obtained by digesting an entire antibody with papain, and a F(ab')2 fragment may be obtained by digesting the antibody with pepsin), and preferably, the antibody fragment may be manufactured through a genetic recombinant technique. In the present invention, the antibody is preferably a Fab type, or an entire antibody. In addition, the heavy chain constant domain may be selected from isotypes including gamma ($\gamma$), mu ($\mu$), alpha ($\alpha$), delta ($\delta$), and epsilon ($\epsilon$) types. The light chain constant domain may be a kappa ($\kappa$) or lambda ($\lambda$) type.

In addition, the antibody of the present invention may be a humanized antibody or a CDR-grafted antibody to further reduce a chimerical antibody or immunogenicity of a chimerical antibody.

The chimerical antibody includes a variable domain derived from animals (for example, a mouse, a rabbit, poultry, etc.) excluding humans, and a constant domain derived from humans. Such a chimerical antibody may be prepared by gene recombination known in the art.

The humanized antibody or CDR-grafted antibody means an antibody prepared by transplanting a complementarity determining region (CDR) of an animal-derived monoclonal antibody in a human antibody to maintain high affinity and specificity of the animal-derived monoclonal antibody and reduce immunity-inducibility, and a humanization degree may be selected in consideration of affinity with respect to an antigen and a degree of inducing immunity in a human body.

The present invention also provides a composition for isolating and purifying a human liver-carboxylesterase 1 protein, comprising the monoclonal antibody of the present invention.

The composition for isolation and purification including the antibody is used in a conventional ion exchange chromatography and affinity chromatography to easily isolate and purify the human liver-carboxylesterase 1 protein from a sample.

The present invention also provides a composition for detecting a human liver-carboxylesterase 1, comprising the monoclonal antibody of the present invention.

The present invention also provides a method of detecting a concentration of a human liver-carboxylesterase 1 in the urine or blood, comprising detecting the formation of an antigen-antibody complex by contacting the monoclonal antibody of the present invention with a sample.

According to the present invention, the human liver-carboxylesterase 1 may be detected by detecting the formation of the antigen-antibody complex by contacting the monoclonal antibody with human urine, serum, or plasma.

The term "antigen-antibody complex" used herein is a combination of the enzyme for confirming the presence or absence of a human liver-carboxylesterase 1 in a biological sample of the human urine, serum, or plasma, and a monoclonal antibody recognizing the enzyme.

The antigen-antibody complex may be detected using a detection label. For example, an enzyme, a fluorescent material, a ligand, a luminous material, a microparticle, a redox molecule, or a radioisotope may be selected, and the present invention is not particularly limited thereto.

For example, the enzyme may be, but is not limited to, β-glucuronidase, β-D-glucosidase, β-D-galactosidase, urease, peroxidase, alkaline phosphatase, acetylcholine esterase, glucose oxidase, hexokinase and GDPase, RNase, glucose oxidase and luciferase, phosphofructokinase, phosphoenolpyruvate carboxylase, aspartate aminotransferase, phosphenolpyruvate decaboxylase, or β-latamase. The fluorescent material may be, but is not limited to, fluorescein, isothiocyanate, rhodamine, picoerythrin, phycocyanin, allophycocyanin, o-phthaldehyde, or fluorescamine. The ligand may be, but is not limited to, a biotin derivative. The luminous material may be, but is not limited to, acridinium ester, luciferin, or luciferase. The microparticle may be, but is not limited to, colloidal gold, or colored latex. The redox molecule may be, but is not limited to, ferrocene, a ruthenium complex, biologen, quinone, a Ti ion, a Cs ion, diimide, 1,4-benzoquinone, hydroquinone, $K_4W(CN)_8$, $[Os(bpy)_3]^{2+}$, $[RU(bpy)_3]^{2+}$, or $[MO(CN)_8]^{4-}$. The radioisotope may be, but is not limited to, $^3H$ $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, or $^{186}Re$.

The formation of the antigen-antibody complex may be detected using a colorimetric method, an electrochemical method, a fluorimetric method, a luminometry method, a particle counting method, a visual assessment method, or a scintillation counting method. For example, the formation of the antigen-antibody complex is detected by flow cytometry, immunocytochemistry, RIA, ELISA, western blotting, immunoprecipitation assay, immunodiffusion assay, complement fixation assay, or a protein chip. More specifically, the formation of the antigen-antibody complex may be detected by immune precipitation and immunoblotting useful to recover small amounts of desired proteins.

The most specifically, the antigen-antibody complex may be detected using ELISA. The ELISA includes various ELISA methods including direct ELISA using a labeled antibody recognizing an antigen attached to a solid support, indirect ELISA using a labeled antibody recognizing a captured antibody in the complex of the antibody recognizing the antigen attached to the solid support, direct sandwich ELISA using another labeled antibody recognizing an antigen in the complex of the antibody attached to the solid support and the antigen, and indirect sandwich ELISA using a labeled secondary antibody recognizing another antibody after the antibody reacts with an antigen in the complex of the antibody attached to the solid support and the antigen.

According to the ELISA detection method, the biological sample such as the urine, blood, serum, or plasma is in contact with the monoclonal antibody of the present invention coated on the solid support, for example, a microtiter plate, a membrane, or a test strip. As a specific example, a well of the microtiter plate is coated with the monoclonal antibody of the present invention, a non-occupied binding site is blocked with, for example, BSA, the well of the coated plate is incubated with a sample, and then the presence of the antigen-antibody complex may be determined. The presence of the antigen-antibody complex may be confirmed using an antibody specific to the antigen of the antigen-antibody complex, for example, a monoclonal or polyclonal antibody specifically binding to the human liver-carboxylesterase 1. The monoclonal or polyclonal antibody may have a detection label, and otherwise, may be confirmed by treating another antibody capable of detecting the monoclonal or polyclonal antibody.

As a particular example, the human liver-carboxylesterase 1 may be detected by reacting the captured monoclonal antibody attached to the support with the biological sample, and measuring a detection labeling signal from the monoclonal antibody specifically binding to the human liver-carboxylesterase 1 or measuring a detection labeling signal from a secondary antibody having a label capable of producing a detectable signal added to the complex.

The present invention also relates to a kit for diagnosing liver cancer, comprising the monoclonal antibody of the present invention.

The monoclonal antibody used in the kit for diagnosing liver cancer of the present invention may also use a fragment of the monoclonal antibody as long as the antibody can selectively recognize the human liver-carboxylesterase 1. Such an antibody fragment may include an F(ab')2, Fab, Fab', or Fv fragment.

The kit for diagnosing liver cancer may be manufactured in a protein chip type to which the monoclonal antibody of the present invention is attached.

In the kit for diagnosing liver cancer of the present invention, a monoclonal antibody selectively recognizing the human liver-carboxylesterase 1 or a fragment thereof, and a tool/reagent used in immunological analysis may be included.

As the tool/reagent used in the immunological analysis, a suitable carrier, labeling material capable of producing a detectable signal, solvent, or washing agent is included. In addition, when the labeling material is an enzyme, a substrate and a reaction stopping agent that can measure enzyme activity may be included.

As a suitable carrier, a soluble carrier, for example, a physiologically available buffer known in the art such as PBS, an insoluble carrier such as polystylene, polyethylene, polypropylene, polyester, polyacrylonitrile, a fluorinated resin, crosslinked dextrane, polysaccharide, a polymer such as a magnetic microparticle in which a metal is plated on a latex, other papers, glass, metal, agarose, or a combination thereof may be used, but the present invention is not limited thereto.

A detection system to be used for the detection method and diagnostic kit of the present invention includes an ELISA plate, a dip-stick device, an immunochromatography test strip, a radioimmunoassay device, and a flow-through device, but the present invention is not limited thereto.

Hereinafter, the present invention will be described in detail by means of Examples. However, it should be understood that the following Example are given by way of illustration of the present invention only, and are not intended to limit the scope of the present invention.

EXAMPLE 1

Supply of Liver Tissue and Plasma Samples 50 mg of liver tissues were put into a cell lysis RIPA buffer [50 mM Tris, 150 mM sodium chloride (NaCl), 1% NonidetP-40, 0.25% sodium deoxycholate, pH 7.4] to be disrupted at 4° C. under a refrigeration condition, and centrifuged at 14000 rpm for 20 minutes to recover a protein solution.

Plasmas dispensed from normal persons, hepatitis patients, cirrhosis patients, and liver cancer patients whose pathological respective data were ensured were provided from the gene bank of Severance Hospital. As the plasmas of the normal persons, samples determined to be negative from liver cancer standard test factors, such as HIV-1 and HIV-2 antibodies derived from human immunodeficiency virus (HIV), a HIV-1 antigen, a hepatitis B surface antigen, a hepatitis B core antigen, a hepatitis C virus, a T cell leukemia virus (HTLV-I/II) antigen, and a Treponema palladium test, were used, and stored at −70° C. before the test. The supply of the plasma was followed by regulations of Institutional Review Board (IRB) of the Yonsei Medical Center.

EXAMPLE 2

Selection of Optimal Antigen Determinant

The selection of a peptide having an optimal antigen determinant in a three-dimensional structure of the liver-carboxylesterase 1 was analyzed using software produced from AbFrontier, and from the analyzed peptide list, it was confirmed that the selected peptide was different from an amino acid sequence of a corresponding protein of a mouse to be immunized. Finally, a peptide having 13 amino acid sequences was synthesized by performing analysis in an actual research and reselection based on a peptide specific to the liver-carboxylesterase 1 (refer to Table 1).

TABLE 1

| Species | Amino acid sequence | (n) | Location of amino acid |
|---|---|---|---|
| Human | KAVEKPPQTEHIEL | 13 | 554-567 |
| Mouse | LRAKKPPQTGHTEL | 13 | 554-567 |

EXAMPLE 3

Immunization of Mouse

In each peptide group, the same amount of auxiliary antigens (Freund's adjuvants) were emulsified to be primarily injected into the abdominal cavity of each of four female BALB/c mice, and after 4 weeks, secondary injection was performed, and after 2 weeks, third injection was performed again to immunize the mouse.

A serum was isolated from the tail of each mouse before each injection, and then a degree of reaction between a peptide antigen and an antibody produced from the mouse was measured by enzyme immunoassay.

Western blotting was performed together to perform analysis at a protein level. Measurement of bindability with the liver-carboxylesterase 1 protein was performed by the western blotting, and as a standard sample, a liver tissue protein was used.

5 µg of a liver tissue protein quantified and added was isolated through 10% SDS-PAGE, and the gel was transferred to a nitrocellulose (NC) membrane and then blocked with a TBS-T buffer containing 5% skimmed milk [20 mM Tris, 137 mM sodium chloride, 0.1% Tween 20, pH 7.6] for 1 hour. A serum of the mouse immunized with a peptide, as a primary antibody, was reacted with 5% skimmed milk in a ratio of 500:1, and as a secondary antibody, an anti-mouse IgG-HRP (Santa Cruz) was reacted in a ratio of 5000:1. The final NC membrane was reacted with an ECL Plus western blot reagent (GE Healthcare) for 3 minutes, and scanned with a Typhoon 9400 scanner to analyze a signal of the liver-carboxylesterase 1 protein reacted by antigen-antibody binding.

Figure 1:
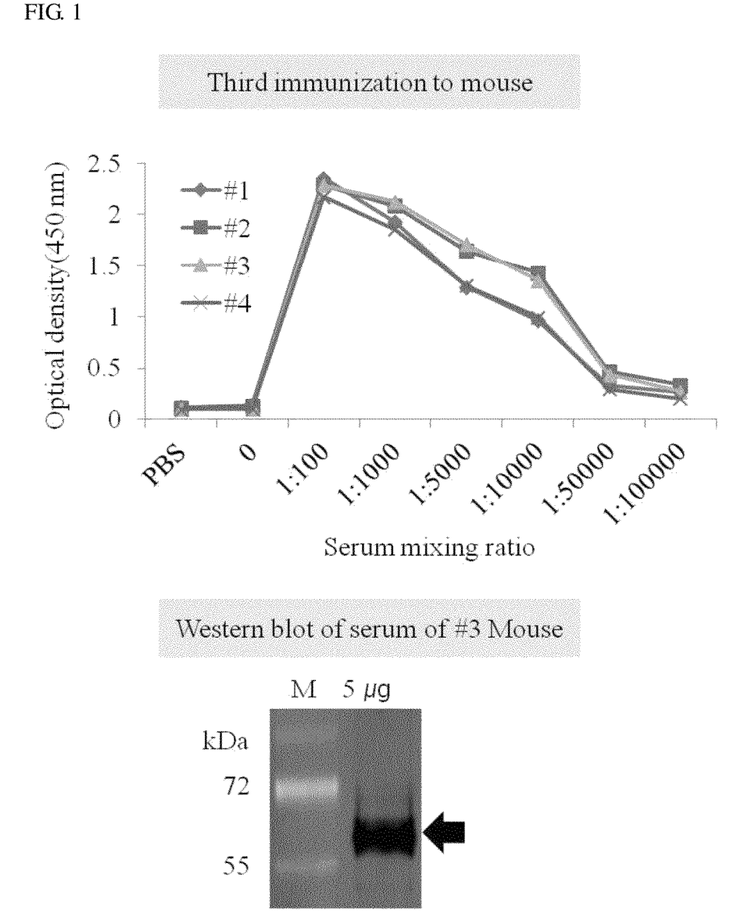
FIG. 1 shows an analysis result of a liver-carboxylesterase 1 by isolating a serum from a tail of a mouse immunized three times with an antigen peptide group.

FIG. 1 is an image showing an analysis diagram of the liver-carboxylesterase 1 in a mouse serum by immunization periods, in which M is a standard marker (5 µg) per molecular weight of a protein, and 5 µg means a liver tissue protein.

As shown in FIG. 1, since #3 mouse showed high antigen-antibody reactivity, the mouse was selected.

EXAMPLE 4

Screening of Optimal Hybridoma Cell Line Producing Monoclonal Antibody

A spleen cell of the #3 mouse selected in Example 3 was isolated to be fused with a Sp2/0-Ag14 myeloma cell, diluted in a HAT medium, and then dispensed into eight 96-well plates to incubate. The incubated cells were subjected to enzyme immunoassay using a peptide synthesized at 250 ng/well as an antigen, and thus 11 wells having the highest optical density were selected. Each cell was incubated in a 24-well, from which 5 wells (#1B2, #1G11, #2F4, #3C1, and #3F2) were selected by the enzyme immunoassay. Each group of the cells was dispensed into a 96-well plate to incubate, and subjected to enzyme immunoassay three times. From the cells, five cloned cells (#1A9, #4H3, #6A10, #8F11, and #10E8) having the highest reactivity were selected.

Figure 2:
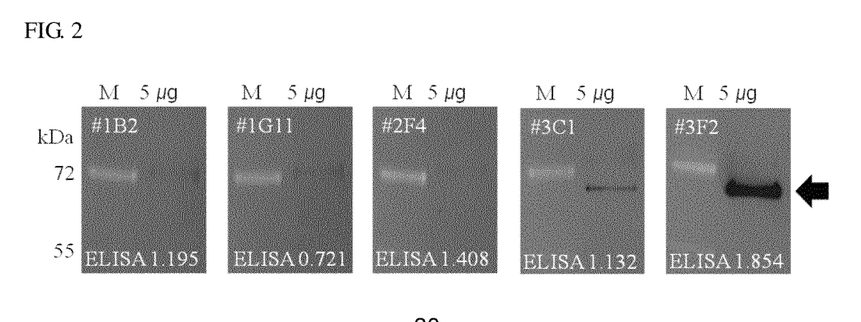
FIG. 2 is an image showing reactivity with respect to a fusion cell between a spleen cell and a myeloma of a mouse immunized to an antigen peptide of a liver-carboxylesterase 1.

FIG. 2 is an image showing a location and binding degree of the liver-carboxylesterase 1, which is a result of western blot analysis for a culture solution of #3 well-cells having a high titration value through the enzyme immunoassay. High reactivity was shown in the #3F2 fusion cell.

Figure 3:
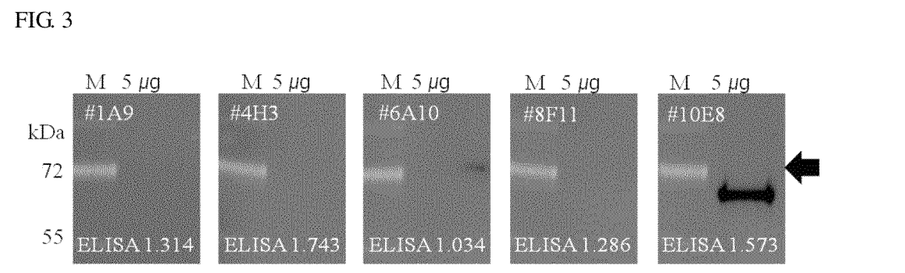
FIG. 3 shows a screening result of a hybridoma cell line producing a monoclonal antibody of a liver-carboxylesterase 1 using a spleen cell of an immunized mouse having high reactivity by an antigen peptide of the liver-carboxylesterase 1.

FIG. 3 is an image showing a result of western blot analysis for cells of a finally-screened well by dispensing cells of five screened #wells into a 96-well plate again, and analyzing the well having a high titration value three times. High reactivity was shown in the #10E8 hybridoma cell.

Accordingly, the #10E8 hybridoma cell line showing high antigen-antibody reactivity was finally selected. After one week, the cells were injected into the abdominal cavity of the mouse. The ascetics were taken from the mouse, concentrated using an antigen-affinity purification column to have a final concentration of 2 mg/ml, and stored in a refrigerator before an experiment.

As the result of measuring a subclass isotype of the final monoclonal antibody #10E8, it was determined as the IgG1 type (refer to Table 2).

TABLE 2

| Clone | IgG1 | IgG2a | IgG2b | IgG3 | IgA | IgM | κ | λ | H-chain | L-chain |
|---|---|---|---|---|---|---|---|---|---|---|
| 10E8 | 0.518 | 0.072 | 0.104 | 0.097 | 0.097 | 0.084 | 0.738 | 0.149 | IgG1 | κ |

EXAMPLE 5

Analysis of Efficiency of Antigen-Antibody Reaction of Monoclonal Antibody: Immunoprecipitation and Immunoblotting Magnetic beads, that is, Dynabead MyOne™ Tosylactivated (Invitrogen), were coated with an anti-liver-carboxylesterase 1 polyclonal antibody (Abcam, #Ab1875) and an anti-liver-carboxylesterase 1 monoclonal antibody (clone #10E8) according to the manufacturer's manual. Each of 10, 20, 30, 40, and 50 μl of the beads to which the anti-liver-carboxylesterase 1 antibody was bound were immunoprecipitated in a 1 ml tube for 2 hours with 100 μg of liver tissue proteins. A protein binding to the antibody was recovered using a PBS-T buffer adjusted to pH 2, and the changes in the binding liver-carboxylesterase 1 of the polyclonal antibody and the monoclonal antibody (clone #10E8) were analyzed using an ImageQuant program through immunoblotting, compared with the polyclonal antibody.

Figure 4:
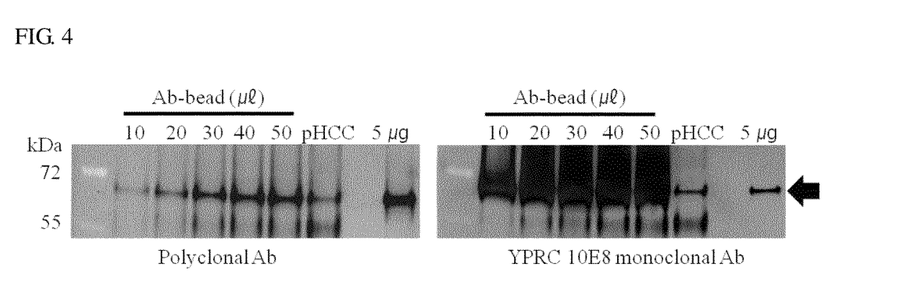
FIG. 4 shows a comparison result of a degree of antigen-antibody binding between a monoclonal antibody of the present invention and a polyclonal antibody of a known liver-carboxylesterase 1.

FIG. 4 shows the comparison of a degree of the antigen-antibody binding between the polyclonal antibody and the monoclonal antibody (clone #10E8). pHCC is 200 μl of a sample in which plasmas of 15 liver cancer patients immunoprecipitated with 30 μl of antibody-binding beads, and 5 μg means a liver tissue protein.

As shown in FIG. 4, under the same conditions, the monoclonal antibody #10E8 showed antigen-antibody reactivity 20 times higher than the polyclonal antibody.

EXAMPLE 6

Analysis of Liver-Carboxylesterase 1 Protein in Plasma Using Monoclonal Antibody: Immunoprecipitation and Immunoblotting Plasmas of each group of 10 normal persons, hepatitis patients, cirrhosis patients, and liver cancer patients were mixed, and 200 μl of each plasma group was immunoprecipitated with the liver-carboxylesterase 1 polyclonal antibody and the monoclonal antibody #10E8 used in Example 5, and subjected to western blot analysis. A signal intensity of the liver-carboxylesterase 1 analyzed when scan resolution was adjusted to 100 microns to perform scanning under the same conditions was analyzed using an ImageQuant program.

Figure 5:
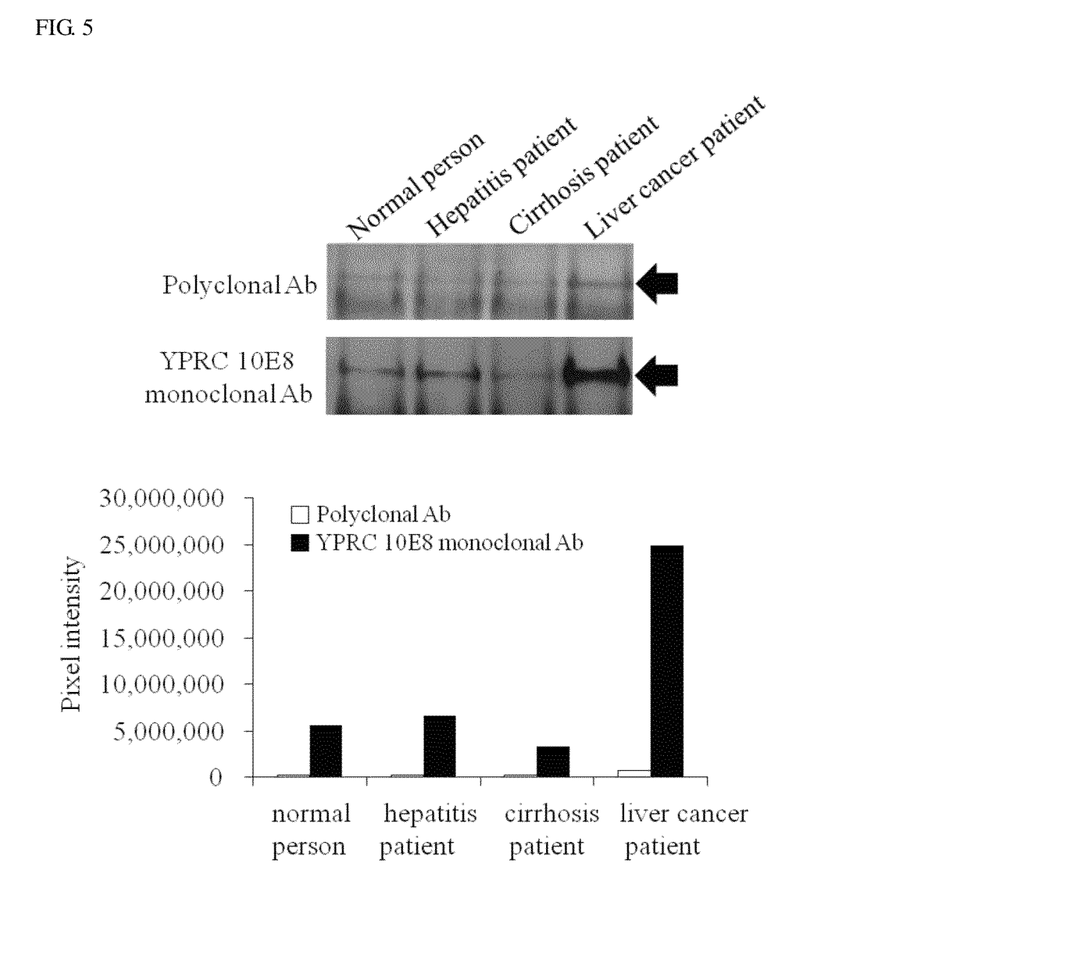
FIG. 5 shows a comparison result of a degree of antigen-antibody binding in plasmas of a normal person, and hepatitis, cirrhosis, and liver cancer patients using a monoclonal antibody of the present invention and a polyclonal antibody of a known liver-carboxylesterase 1.

As shown in FIG. 5 and Table 3, it was confirmed that the intensity of the liver-carboxylesterase 1 binding to the monoclonal antibody was increased by 30 times or more on average, compared to when the polyclonal antibody was used.

TABLE 3

| Kinds of antibody | Normal person | Hepatitis patient | Cirrhosis patient | Liver cancer patients |
|---|---|---|---|---|
| Polyclonal antibody | 191,363 | 182,431 | 178,140 | 738,366 |
| Monoclonal antibody | 5,586,315 | 6,676,570 | 3,314,999 | 24,906,430 |

EXAMPLE 7

Analysis of Liver-Carboxylesterase 1 Protein in Plasma Using Monoclonal Antibody: ELISA 200 μl each of the monoclonal antibody #10E8 diluted in a concentration of 0.5 mg/ml, and two polyclonal antibodies 1 and 2 (#Ab1875, #Ab77730) prepared by Abcam that enabled ELISA was added to a 96-well plate. After the antibodies added to the 96-well plate were reacted in a refrigerator for 10 hours, 200 μl of a sample in which a standard protein of the liver-carboxylesterase 1 was mixed as a comparative sample was added to the well, and reacted for 2 hours. As a secondary binding antibody, an HRP enzyme-binding hCE1 antibody (#Ab34595) was added in a ratio of 5000:1 and reacted for 1 hour, and a TMB coloring reagent was added.

Figure 6:
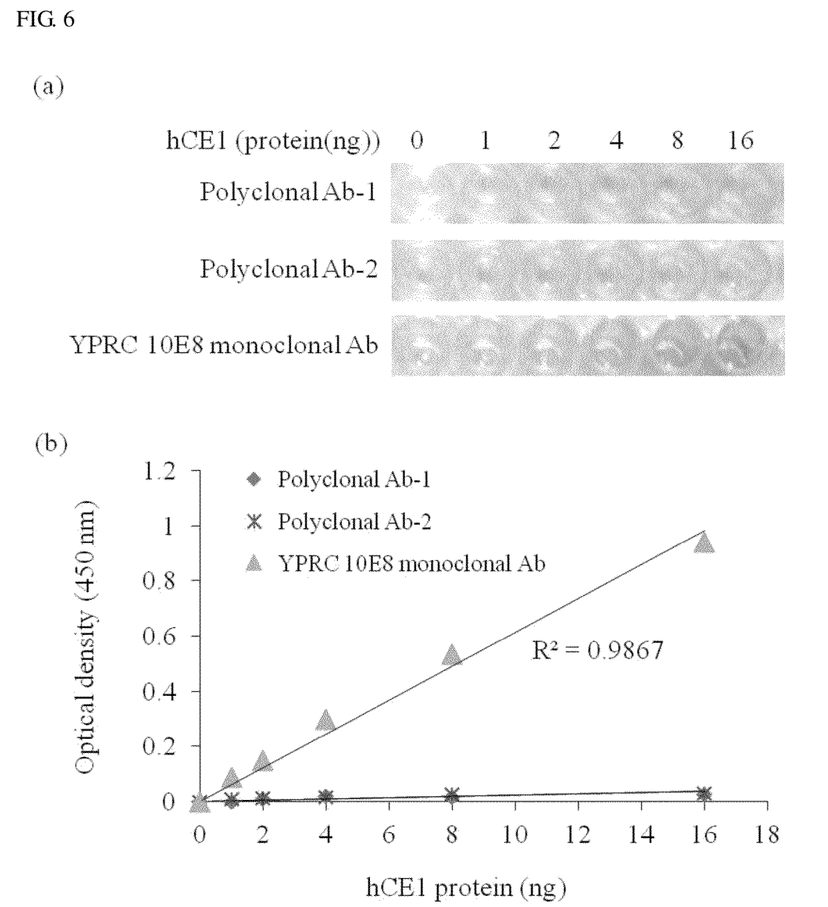
FIG. 6 shows (a) a coloring result of samples according to antigen-antibody binding using a monoclonal antibody of the present invention and a polyclonal antibody of a known liver-carboxylesterase 1, and (b) optical density values according to antigen-antibody binding by concentrations of the liver-carboxylesterase 1.

FIG. 6 is the comparison result of a degree of antigen-antibody binding between the monoclonal antibody #10E8 and the two polyclonal antibodies 1 and 2 (#Ab1875, #Ab77730) prepared by Abcam that enabled ELISA, which shows (a) a coloring result of the samples according to the antigen-antibody binding, and (b) optical densities according to the antigen-antibody binding by concentrations of the liver-carboxylesterase 1.

As shown in FIG. 6, comparing the optical densities obtained by analysis of a standard curve, it was confirmed that the #10E8 antibody of the present invention had considerably higher efficiency of binding the monoclonal antibody than the same content of an antibody.

A monoclonal antibody of a human liver-carboxylesterase 1 according to the present invention can be used to probe the liver-carboxylesterase 1 in a tissue, cell, or the blood due to highly specific binding to a human liver-carboxylesterase 1 protein. Particularly, the monoclonal antibody can be useful to simply diagnose liver cancer from the blood in an early stage.

The present invention can be used in a protein or disease diagnosis field.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. A monoclonal antibody specifically binding to a human liver-carboxylesterase 1 protein, which is produced by a hybridoma deposited under Accession No. KCLRF-BP-00282.

2. The monoclonal antibody according to claim 1, which recognizes an epitope sequence of amino acids 554 to 567 at the C-terminal of the human liver-carboxylesterase 1 protein.

3. The monoclonal antibody according to claim 1, which is an immunoglobulin isotype of IgG1.

4. A hybridoma cell deposited under Accession No. KCLRF-BP-00282, which produces the monoclonal antibody of claim 1.

5. A composition for isolating and purifying a human liver-carboxylesterase 1 protein, comprising the monoclonal antibody of claim 1.

6. A composition for detecting a human liver-carboxylesterase 1, comprising the monoclonal antibody of claim 1.

7. A method of detecting a concentration of a human liver-carboxylesterase 1 in the urine or blood sample, comprising detecting the formation of an antigen-antibody complex by contacting the monoclonal antibody of claim 1 with said sample.

8. A kit for diagnosing liver cancer, comprising the monoclonal antibody of claim 1.

* * * * *

SEQUENCE LISTING

```
<160> NUMBER OF SEQ ID NOS: 2

<210> SEQ ID NO 1
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: Liver carboxylesterase 1 c-terminal 554-567
      aa from Homo sapiens
```

```
<400> SEQUENCE: 1

Lys Ala Val Glu Lys Pro Pro Gln Thr Glu His Ile Glu Leu
1               5                   10

<210> SEQ ID NO 2
<211> LENGTH: 14
<212> TYPE: PRT
<213> ORGANISM: Mus musculus
<220> FEATURE:
<221> NAME/KEY: MISC_FEATURE
<222> LOCATION: (1)..(14)
<223> OTHER INFORMATION: Liver carboxylesterase 1 c-terminal 554-567
      aa from Mus musculus

<400> SEQUENCE: 2

Leu Arg Ala Lys Lys Pro Pro Gln Thr Gly His Thr Glu Leu
1               5                   10
```